US012322501B2

(12) United States Patent
Masson et al.

(10) Patent No.: US 12,322,501 B2
(45) Date of Patent: Jun. 3, 2025

(54) SYSTEM AND METHOD FOR MANAGING A MEDICAL PROCEDURE ROOM

(71) Applicant: EXPANDED EXISTENCE, INC., Windermere, FL (US)

(72) Inventors: Robert L. Masson, Windermere, FL (US); Raymond G. Oktavec, Fort Lauderdale, FL (US); Douglas Sonders, Ashburn, VA (US); Nicholas Cambata, Ashburn, VA (US); Kyle A. Masson, Windermere, FL (US); Vavao Burge, Mount Dora, FL (US)

(73) Assignee: Expanded Existence Inc., Windermere, FL (US)

( * ) Notice: Subject to any disclaimer, the term of this patent is extended or adjusted under 35 U.S.C. 154(b) by 298 days.

(21) Appl. No.: 18/309,361

(22) Filed: Apr. 28, 2023

(65) Prior Publication Data
US 2024/0363232 A1    Oct. 31, 2024

(51) Int. Cl.
*G16H 40/20* (2018.01)
*G06T 7/70* (2017.01)
*G06T 19/00* (2011.01)

(52) U.S. Cl.
CPC ............. *G16H 40/20* (2018.01); *G06T 7/70* (2017.01); *G06T 19/00* (2013.01);
(Continued)

(58) Field of Classification Search
CPC ........... G16H 40/20; G06T 7/70; G06T 19/00; G06T 2200/24; G06T 2207/30004; G06T 2210/41
(Continued)

(56) References Cited

U.S. PATENT DOCUMENTS

2017/0239000 A1* 8/2017 Moctezuma de la Barrera .......... G16H 40/40
2018/0357825 A1* 12/2018 Hofmann ................ A61B 34/20
(Continued)

FOREIGN PATENT DOCUMENTS

CN    106920451 A    7/2017
CN    109758230 B    4/2021

OTHER PUBLICATIONS

International Search Report dated Jul. 12, 2024 issued in PCT International Application No. PCT/US2024/22010, filed Mar. 28, 2024.

*Primary Examiner* — Hai Tao Sun
(74) *Attorney, Agent, or Firm* — Sagacity Legal PLLC

(57) ABSTRACT

A system for managing medical procedure room for medical procedure comprising a computing device and an augmented reality device. The computing device is configured to execute a creator module to obtain spatial information corresponding to physical characteristics of medical procedure room, generate virtual map, display virtual map, and insert virtual representations of medical items into virtual map. The computing device is configured to execute the creator module to determine position data of the virtual representations in the virtual map and associate the position data with a medical practitioner identifier, a medical procedure identifier, and a medical procedure room identifier. The augmented reality device is configured to execute an experience module to obtain a reality view of medical procedure room, associate spatial information with reality view, determine locations of virtual representations in reality view based on the position data, and superimpose virtual representations at the locations in the reality view.

16 Claims, 10 Drawing Sheets

(52) U.S. Cl.
CPC ............... *G06T 2200/24* (2013.01); *G06T 2207/30004* (2013.01); *G06T 2210/41* (2013.01)

(58) Field of Classification Search
USPC ........................................ 345/633
See application file for complete search history.

(56) References Cited

U.S. PATENT DOCUMENTS

| | | |
|---|---|---|
| 2020/0126661 A1 | 4/2020 | Flexman et al. |
| 2021/0225502 A1* | 7/2021 | Wright .................. G16H 40/63 |
| 2022/0223268 A1 | 7/2022 | Masson et al. |
| 2022/0384019 A1 | 12/2022 | Shelton, IV et al. |

* cited by examiner

SYSTEM AND METHOD FOR MANAGING A MEDICAL PROCEDURE ROOM

BACKGROUND OF THE INVENTION

According to data from the United States Surgical Procedures Market Report 2022, over one hundred (100) million surgical procedures were performed in 2022 in the United States alone, and that number continues to grow. The setup of the medical procedure room is one of the most important factors for medical practitioner efficiency, patient safety, and team workflow. The setup of a medical procedure room should be optimized for efficiency and procedure predictability.

Before a medical procedure begins, the medical procedure room setup must be carefully planned as there is not a "one size fits all" approach to medical procedure room setup. The medical procedure room must be equipped with an adequate number, and the right type, of supplies and tools, such as surgical instruments, lights, trays, robotic systems, anesthetic systems, scalpels and blades, and reusable and disposable supplies. Not only must the fixed or semi-fixed equipment be properly arranged prior to the commencement of the procedure, but chargeable supplies (for example, sutures, sponges, clips, medical implants, screws, rods, arthroplasty devices, stimulators, needles, scalpel blades, catheters, drill bits) and disposable supplies (for example, gauze, gloves, liners, needles, syringes, and tubing) should be carefully tracked for billing and supply analysis and inventory management.

Accordingly, medical procedure room setup can be a complicated and time-consuming exercise that is prone to human error and failure to achieve optimization.

BRIEF DESCRIPTION OF THE SEVERAL VIEWS OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Figure 1:
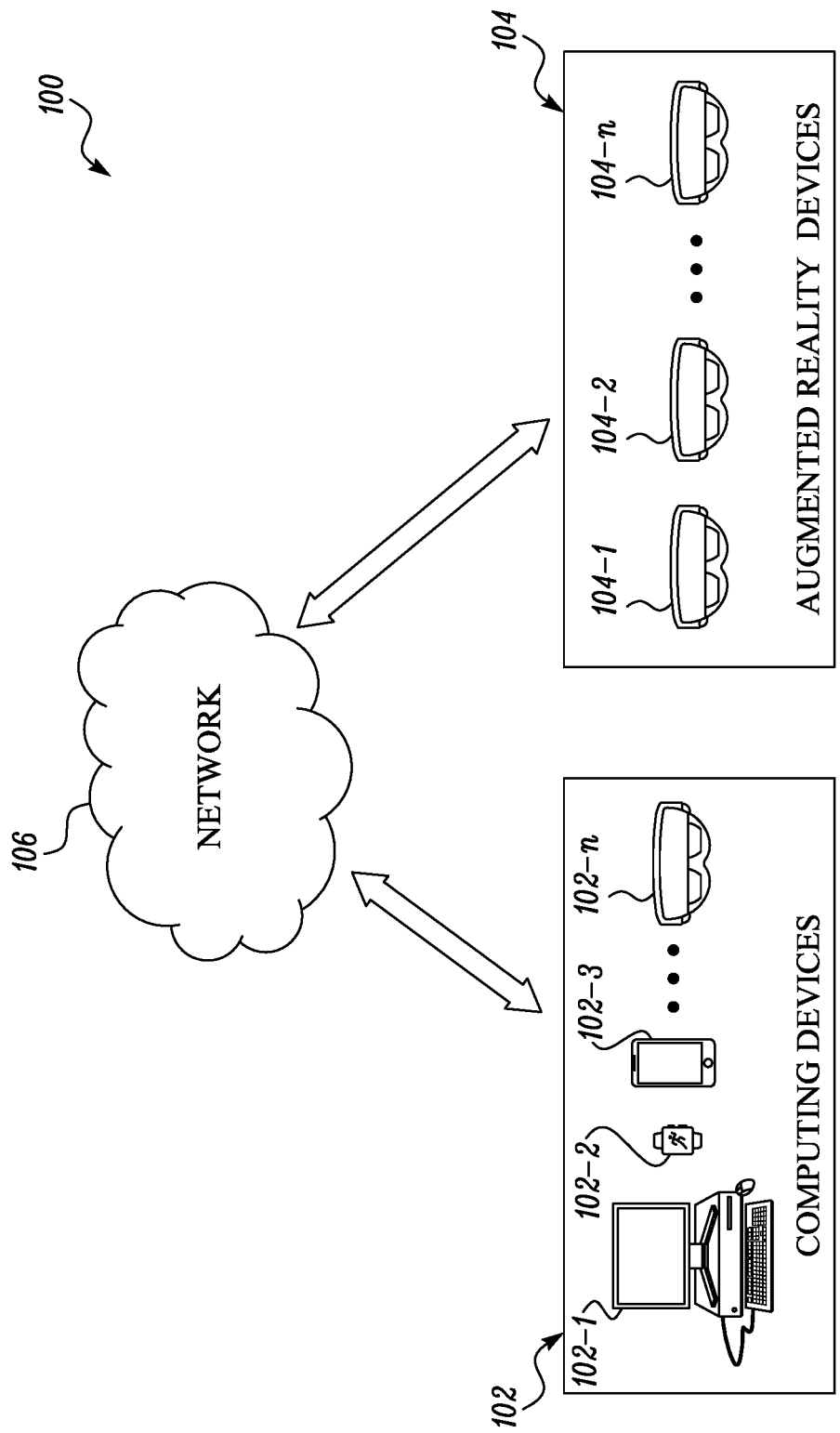
FIG. 1 is a block diagram of a system for managing a medical procedure room for a medical procedure, in accordance with some embodiments.

Skilled artisans will appreciate that the elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE INVENTION

In one aspect, a system for managing a medical procedure room for a medical procedure is described. The system includes a computing device and an augmented reality device communicatively coupled to the computing device. The computing device is configured to execute a creator module to obtain a spatial information corresponding to physical characteristics of the medical procedure room and generate a virtual map of the medical procedure room based on the spatial information. The computing device is further configured to execute the creator module to display, on a computing device display, the virtual map of the medical procedure room and insert, via a computing device user interface, one or more virtual representations of one or more medical items into the virtual map of the medical procedure room in response to one or more commands. The computing device is further configured to execute the creator module to determine position data of the one or more virtual representations in the virtual map with respect to the virtual map and associate the position data with a medical practitioner identifier identifying the medical practitioner, a medical procedure identifier identifying the medical procedure, and a medical procedure room identifier identifying the medical procedure room. The computing device is further configured to execute the creator module to transmit, via a computing device transceiver, the position data associated with the medical practitioner identifier, the medical procedure identifier, and the medical procedure room identifier. The augmented reality device is configured to execute an experience module to obtain a reality view of the medical procedure room and associate the spatial information with the reality view of the medical procedure room. The augmented reality device is further configured to execute the experience module to receive, via an augmented reality device transceiver, the position data and co-relate and determine locations of the one or more virtual representations in the reality view based on the position data. The augmented reality device is further configured to execute the experience module to superimpose, on an augmented reality device display, the one or more virtual representations at the locations in the reality view, monitor physical features of the medical procedure room over a period for which the medical practitioner performs the medical procedure in the medical procedure room and obtain a first data. The augmented reality device is further configured to execute the experience module to pursuant to a lapse of the period, provide via the augmented reality device transceiver the first data to the computing device to provide recommendations, on the computing device display, to modify the one or more virtual representations in the virtual map of the medical procedure room corresponding to the medical practitioner identifier, the medical procedure identifier, and the medical procedure room identifier.

In another aspect, a method for managing a medical procedure room for a medical procedure is described. The method includes obtaining, by a computing device, a spatial information corresponding to physical characteristics of the medical procedure room and generating, by the computing device, a virtual map of the medical procedure room based on the spatial information. The method further includes displaying, by the computing device, the virtual map of the medical procedure room on a computing device display and inserting, by the computing device, one or more virtual representations of one or more medical items into the virtual map of the medical procedure room in response to one or more commands. Further, the method includes determining, by the computing device, position data of the one or more virtual representations in the virtual map with respect to the virtual map and associating, by the computing device, the position data with a medical practitioner identifier identifying the medical practitioner, a medical procedure identifier identifying the medical procedure, and a medical procedure room identifier identifying the medical procedure room. The method further includes transmitting, by the computing device, the position data associated with the medical practitioner identifier, the medical procedure identifier, and the medical procedure room identifier via a computing device transceiver, obtaining, by an augmented reality device, a reality view of the medical procedure room, and associating, by the augmented reality device, the spatial information with the reality view of the medical procedure room. Further, the method includes receiving, by the augmented reality device, the position data via an augmented reality device transceiver, co-relating and determining, by the augmented reality device, locations of the one or more virtual representations in the reality view based on the position data, and superimposing, by the augmented reality device, the one or more virtual representations at the locations in the reality view on an augmented reality device display. The method further includes monitoring, by the augmented reality device, physical features of the medical procedure room over a period for which the medical practitioner performs the medical procedure in the medical procedure room and obtaining a first data and pursuant to a lapse of the period, providing, by the augmented reality device, the first data to the computing device to provide recommendations on the computing device display to modify the one or more virtual representations in the virtual map of the medical procedure room corresponding to the medical practitioner identifier, the medical procedure identifier, and the medical procedure room identifier.

FIG. 1 is a block diagram of a system 100 for managing a medical procedure room for a medical procedure in accordance with various embodiments. In an embodiment, the medical procedure room is a room used for performing one or more medical procedures and includes one or more medical items associated with the medical procedures. For example, the medical procedure room includes the medical items now known or in the future developed, such as, but not limited to, a medical procedure table, one or more auxiliary tables or stands (such as a Mayo stand), one or more storage closets, nurse workstations, back tables, anesthesia systems, electrocautery systems, enabling technology systems or workstations (for example, but not limited to, microscopes, robotic surgical systems, networked robotics, illumination systems, or the like, and accompanying monitors or displays), biometric readers, and/or wireless transceivers.

In accordance with various embodiments, the management of the medical procedure room includes a set-up of the medical items in the medical procedure room. The set-up of the medical items includes the position and orientation of the medical items in the medical procedure room. The system 100 provides for the set-up of the medical items that are specific for a medical practitioner for a specific medical procedure in a specific medical procedure room, using one or more augmented reality devices, as will be described further in accordance with some embodiments. To this end, the system 100 for managing the medical procedure room includes one or more computing devices 102 (for example, but not limited to, computing devices 102-1, 102-2, 102-3 . . . 102-n) and one or more augmented reality devices 104 (for example, but not limited to, augmented reality devices 104-1, 104-2, . . . 104-n). Communication between the one or more computing devices 102 and the one or more augmented reality devices 104, in some embodiments, occurs through the network 106. In some embodiments, the network 106 is, for example, a wide area network (WAN) (for example, a transport control protocol/internet protocol (TCP/IP) based network), a cellular network, or a local area network (LAN) employing any of a variety of communications protocols as is well known in the art or developed in future. In some embodiments, the connection between the one or more computing devices 102 and the one or more augmented reality devices 104 is an intermittent connection. In such cases, the one or more computing devices 102 and the one or more augmented reality devices 104 are configured to download and store the data required to perform their respective functions/operations (as described in detail in the description herein) when the connection is established.

Figure 2:
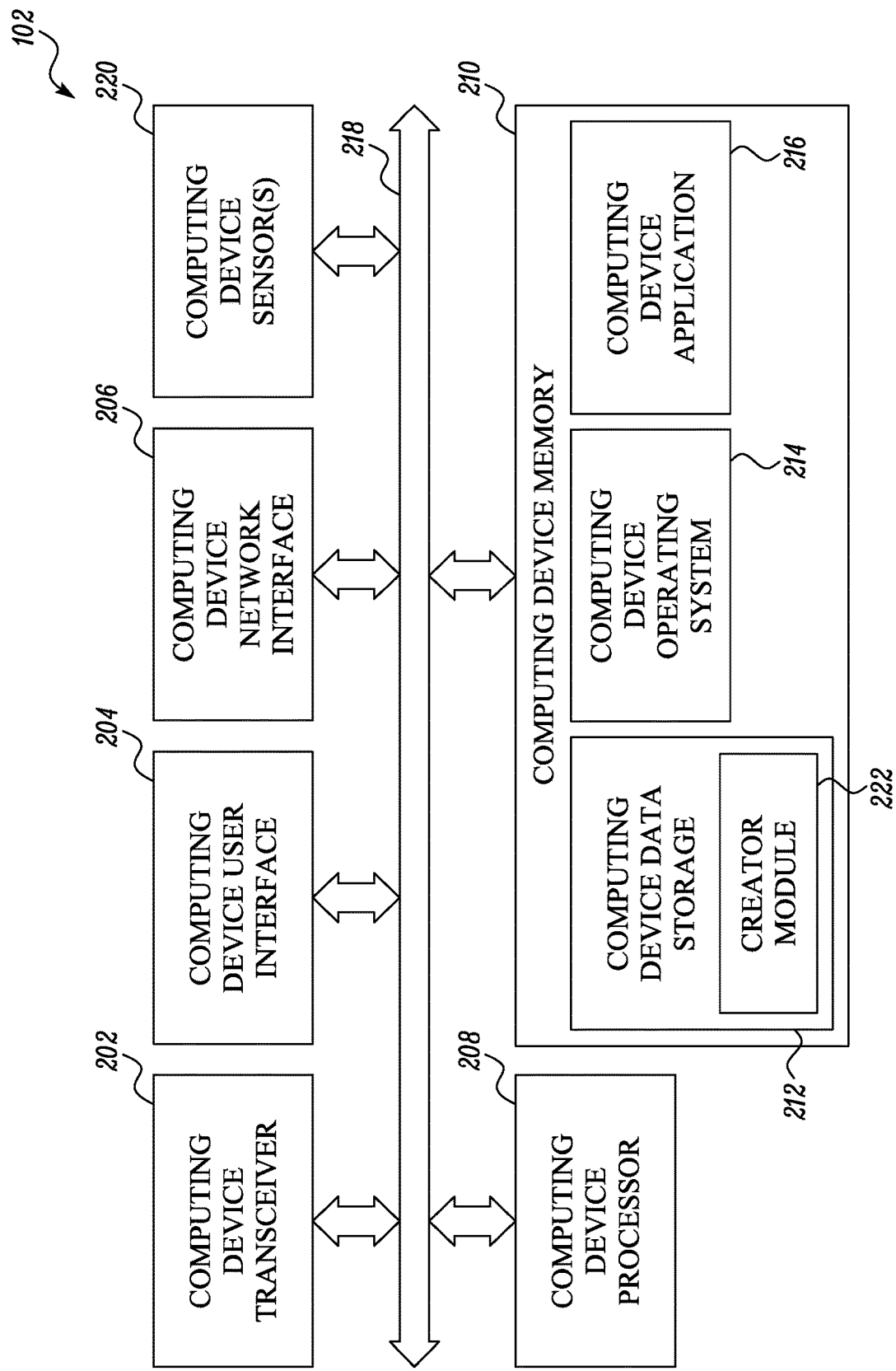
FIG. 2 is a block diagram of a computing device for use within the system of FIG. 1, in accordance with some embodiments.

In some embodiments, each of the one or more computing devices 102 operates as a user interface for one or more users, such as a medical procedure room personnel or a medical practitioner, for management of the medical procedure room as will be further described with respect to FIG. 2. For ease of reference, the components and the functionality of one computing device 102 are described hereinafter, however same components and functionality are applicable to other computing devices 102 shown in FIG. 1.

Figure 3:
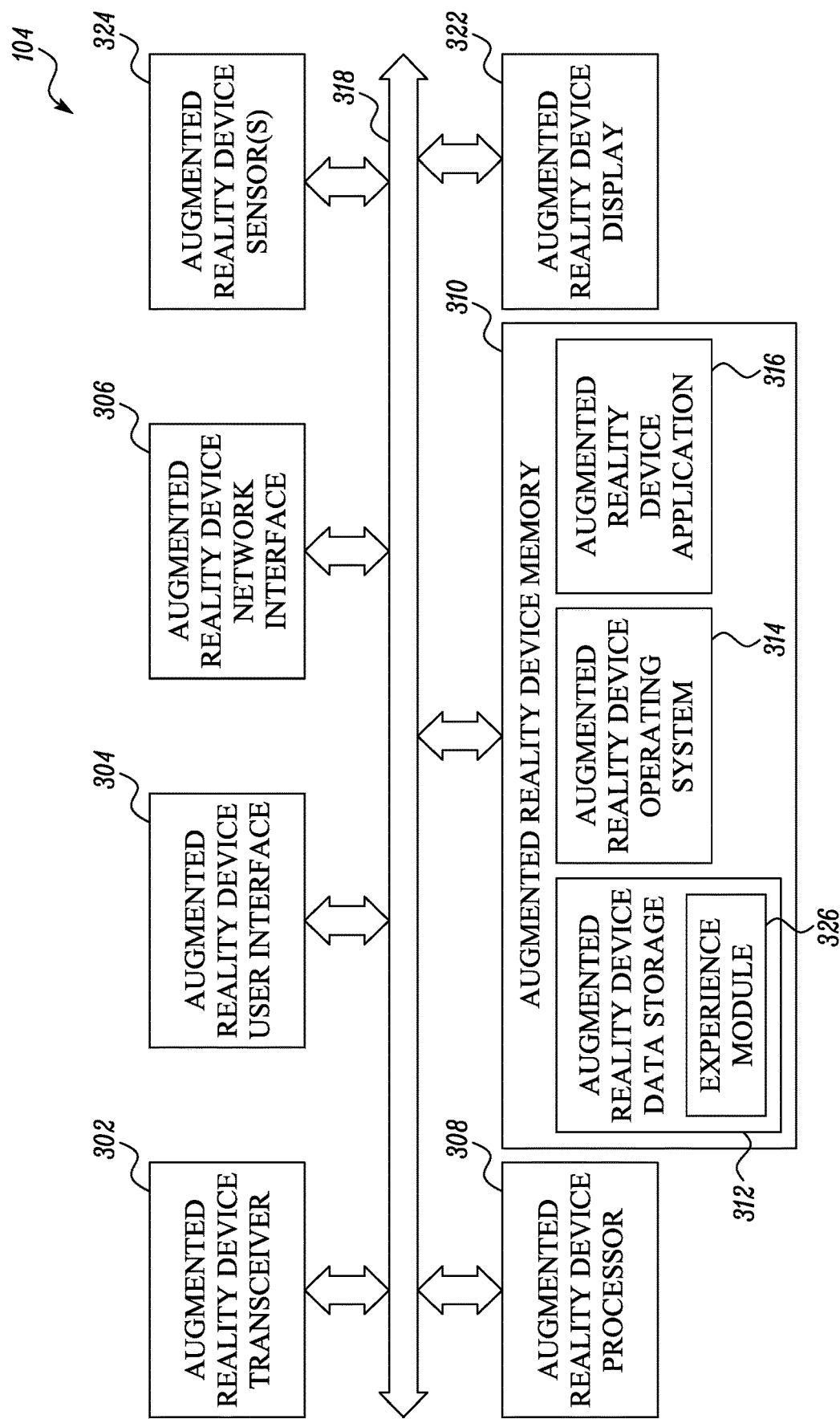
FIG. 3 is a block diagram of an augmented reality device for use within the system of FIG. 1, in accordance with some embodiments.

In some embodiments, each of the one or more augmented reality devices 104 further operates as a user interface for one or more users, such as a medical procedure room personnel or a medical practitioner, for management of the medical procedure room as will be further described with respect to FIG. 3. For ease of reference, the components and the functionality of one augmented reality device 104 are described hereinafter, however same components and functionality are applicable to other augmented reality devices 104 shown in FIG. 1.

FIG. 2 is a block diagram of one exemplary embodiment of a computing device 102 for use within the system 100 of FIG. 1 in accordance with some embodiments. The computing device 102 is electrically and/or communicatively connected to the augmented reality devices 104. In some embodiments, the computing device 102 includes a plurality of electrical and electronic components, providing power, operational control, communication, and the like within the computing device 102. For example, in one embodiment, the computing device 102 includes, among other things, a computing device transceiver 202, a computing device user interface 204, a computing device network interface 206, a computing device processor 208, a computing device memory 210, and one or more computing device sensors 220.

It should be appreciated by those of ordinary skill in the art that FIG. 2 depicts the computing device 102 in a simplified manner and a practical embodiment may include additional components and suitably configured logic to support known or conventional operating features that are not described in detail herein. It will further be appreciated by those of ordinary skill in the art that the computing device 102 is a personal computer, a desktop computer, a tablet, an augmented reality device, a smartphone, a wearable device (wrist worn, eye worn, and the like), or any other computing device now known or in the future developed. It will further be appreciated by those of ordinary skill in the art that the computing device 102 alternatively functions within a remote server, cloud computing device, or any other remote computing mechanism now known or in the future developed.

The components of the computing device 102 (for example 202, 204, 206, 208, 210, and 220) are communicatively coupled via a computing device local interface 218. The computing device local interface 218 includes, for example but not limited to, one or more buses or other wired or wireless connections, as is known in the art. In an embodiment, the computing device local interface 218 has additional elements, which are omitted for simplicity, such as controllers, buffers (caches), drivers, repeaters, and receivers, among many others, to enable communications. Further, in some embodiments, the computing device local interface 218 includes address, control, and/or data connections to enable appropriate communications among the aforementioned components.

The computing device processor 208 is a hardware device for executing software instructions. In an embodiment, the computing device processor 208 is any custom made or commercially available processor, a central processing unit (CPU), an auxiliary processor among several processors associated with the computing device processor 208, a semiconductor-based microprocessor, or generally any device for executing software instructions now known or in the future developed. When the computing device 102 is in operation, the computing device processor 208 is configured to execute software stored within the computing device memory 210, to communicate data to and from the computing device memory 210, and to generally control operations of the computing device 102 pursuant to the software instructions. The detailed functionalities and operations of the computing device processor 208 will be described hereinafter in greater detail.

The computing device user interface 204 is used to receive user input from and/or for providing system output to the user (for example, the medical procedure room personnel or the medical practitioner) or to one or more devices. User input is provided via, for example, a keyboard, touchpad, a mouse, and/or any other user input now known or in the future developed, or any combination thereof. System output is provided via a computing device display, speakers, a printer (not shown) and/or any other system output now known or in the future developed, or any combination thereof. The computing device user interface 204 further includes, for example, a serial port, a parallel port, an infrared (IR) interface, a universal serial bus (USB) interface, and/or any other interface now known or in the future developed.

The computing device network interface 206 is used to enable the computing device 102 to communicate on a network, such as, the network 106 of FIG. 1, a wireless access network (WAN), a radio frequency (RF) network, and the like. The computing device network interface 206 includes, for example, an Ethernet card or adapter or a wireless local area network (WLAN) card or adapter. Additionally, or alternatively, the computing device network interface 206 includes a radio frequency interface for wide area communications such as Long-Term Evolution (LTE) networks, or any other network now known or in the future developed. In an embodiment, the computing device network interface 206 includes address, control, and/or data connections to enable appropriate communications on the network.

The computing device memory 210 includes any non-transitory memory elements comprising one or more of volatile memory elements (for example, random access memory (RAM), nonvolatile memory elements (for example, read-only memory "ROM"), and combinations thereof). Moreover, the computing device memory 210 incorporates electronic, magnetic, optical, and/or other types of storage media now known or in the future developed. Note that, in some embodiments, the computing device memory 210 has a distributed architecture, where various components are situated remotely from one another, but are accessed by the computing device processor 208. The software in the computing device memory 210 includes one or more software programs, each of which includes an ordered listing of executable instructions for implementing logical functions. The software in the computing device memory 210 includes a computing device operating system 214 and one or more computing device applications 216. The computing device operating system 214 controls the execution of other computer programs, such as, the one or more computing device applications 216, and provides scheduling, input-output control, file and data management, memory management, and communication control and related services. The one or more computing device applications 216 are configured to implement the various processes, algorithms, methods, techniques, and the like described herein.

The computing device memory 210 includes a creator module 222 that is executed by the computing device processor 208 to implement the various processes, algorithms, methods, techniques, and the like described herein. The computing device memory 210 further includes a computing device data storage 212 used to store data. In the exemplary embodiment of FIG. 2, the computing device data storage 212 is located internal to the computing device memory 210 of the computing device 102. Additionally, or alternatively (not shown), the computing device data storage 212 is located external to the computing device 102 such as, for example, an external hard drive connected to the computing device user interface 204. In some embodiments (not shown), the computing device data storage 212 is located external and connected to the computing device 102 through a network and accessed via the computing device network interface 206. In some embodiments, when the connection between the computing device 102 and the augmented reality device 104 is an intermittent connection, the data is stored in the computing device data storage 212. Alternatively, when the connection between the computing device 102 and the augmented reality device 104 is constant (not intermittent), the data is stored within one or more of the computing device data storage 212, any memory external to the computing device 102, and/or distributed thereto.

In operation, information for storage in the computing device data storage 212 is entered via the computing device user interface 204. Alternatively, information for storage in the computing device data storage 212 is received from the augmented reality device 104 via the computing device transceiver 202. Alternatively, information for storage in the computing device data storage 212 is received from one or more sensors (not shown) external to the computing device 102 via the computing device transceiver 202 or the computing device sensors 220. For example, spatial information corresponding to physical characteristics of one or more medical procedure rooms, virtual maps of the one or more medical procedure room, virtual representations of the medical items, position data associated with placement of the virtual representations of the medical items with respect to the virtual map, association of the position data with a medical practitioner identifier identifying the medical practitioner, a medical procedure identifier identifying the medical procedure, and a medical procedure room identifier identifying the medical procedure room, and the like, are stored in the computing device data storage 212.

The computing device 102 in the illustrated example includes the computing device transceiver 202. The computing device transceiver 202 incorporating within a computing device transceiver antenna (not shown), enables wireless communication between the computing device 102 and other devices, for example, the augmented reality device 104. It will be appreciated by those of ordinary skill in the art that the computing device 102 includes a single computing device transceiver 202 as shown, or alternatively separate transmitting and receiving components, for example, but not limited to, a transmitter, a transmitting antenna, a receiver, and a receiving antenna and/or any combination thereof.

The computing device 102 in the illustrated example includes one or more computing device sensors 220. The one or more computing device sensors 220 detect the spatial information corresponding to the physical characteristics of the medical procedure room. It will be appreciated by those of ordinary skill in the art that the one or more computing device sensors 220 utilize any sensor technology now known or in the future developed. For example, the computing device sensors 220 include one or more of a Light Detection and Ranging (LiDAR) sensor, a Radio Detection and Ranging (RADAR), ultrasonic sensors, three-dimensional (3D) scanner, IoT (Internet of Things) sensors, RFID (radio frequency identification) sensors, image sensors (for example, camera), Quick Response (QR) code readers, biometric sensors, and various other sensors known in the art or developed in future. In some embodiments, the computing device sensors 220 include one or more sensors, such as, accelerometers, gyroscopes, and magnetometers to track the orientation and movement of the computing device 102. Each of the one or more computing device sensors 220 comprises a detector allowing the detection of spatial information corresponding to the physical characteristics of the medical procedure room and/or various medical items contained within. In operation, the one or more computing device sensors 220 communicate with one another, with other sensors within the medical procedure room, and/or with any other device within or external to the medical procedure room. In some embodiments, the computing device sensors 220 are physically within, co-located, or external to the computing device 102.

FIG. 3 is a block diagram of one exemplary embodiment of the augmented reality device 104 for use within the system 100 of FIG. 1 in accordance with some embodiments. The augmented reality device 104 provides an augmented reality interface in which a direct or indirect view of real-world environments, for example, the medical procedure room, in which the user of the augmented reality device 104 is currently disposed are augmented (for example, supplemented, by additional sensory input such as sound, images, graphics, or other information, generated by the computing device 102). In still other embodiments, the augmented reality device 104 provides a mixed reality interface in which electronically generated objects, for example, virtual representations of the medical items, are inserted in a direct or indirect view of real-world environments in a manner such that they co-exist and interact in real time with the real-world environment and real-world objects of the medical procedure room. It will be appreciated by those of ordinary skill in the art that the augmented reality device 104 comprises any augmented reality, mixed reality, or virtual reality technology now known or in the future developed.

The augmented reality device 104 is electrically and/or communicatively connected to a variety of other devices, for example, the computing devices 102, as previously described with respect to FIG. 1 herein. In some embodiments, the augmented reality device 104 includes a number of electrical and electronic components, providing power, operational control, communication, and the like within the augmented reality device 104. For example, the augmented reality device 104 in one embodiment includes, among other things, an augmented reality device transceiver 302, an augmented reality device user interface 304, an augmented reality device network interface 306, an augmented reality device processor 308, an augmented reality device memory 310, one or more augmented reality device sensors 324, and an augmented reality device display 322.

It should be appreciated by those of ordinary skill in the art that FIG. 3 depicts the augmented reality device 104 in a simplified manner and a practical embodiment includes additional components and suitably configured logic to support known or conventional operating features that are not described in detail herein. It will further be appreciated by those of ordinary skill in the art that the augmented reality device 104 is a head-mounted display device in the form of eyeglasses, goggles, a helmet, a visor, or any other augmented reality device eyewear now known or in the future developed. It will further be appreciated by those of ordinary skill in the art that the augmented reality device 104 generates and/or displays augmented reality images. In the augmented reality device 104, a scene produced on a display device is oriented or modified based on user input. The augmented reality device 104 provides a visual image in which a reality view of the medical procedure room and the virtual representation of medical items are presented together within a single display, such as, the augmented reality device display 322.

The components of the augmented reality device 104 (for example 302, 304, 306, 308, 310, 322, 324) are communicatively coupled via an augmented reality device local interface 318. The augmented reality device local interface 318 includes, for example, but not limited to, one or more buses or other wired or wireless connections, as is known in the art. In an embodiment, the augmented reality device local interface 318 has additional elements, which are omitted for simplicity, such as controllers, buffers (caches), drivers, repeaters, and receivers, among many others, to enable communications. Further, in some embodiments, the augmented reality device local interface 318 includes address, control, and/or data connections to enable appropriate communications among the aforementioned components.

The augmented reality device processor 308 is a hardware device for executing software instructions now known or in the future developed. In an embodiment, the augmented reality device processor 308 is any custom-made or commercially available processor, a central processing unit (CPU), an auxiliary processor among several processors associated with the augmented reality device processor 308, a semiconductor-based microprocessor, or generally any device for executing software instructions. When the augmented reality device 104 is in operation, the augmented reality device processor 308 is configured to execute software stored within the augmented reality device memory 310, to communicate data to and from the augmented reality device memory 310, and to generally control operations of the augmented reality device 104 pursuant to the software instructions. The detailed functionalities and operations of the augmented reality device processor 308 will be described hereinafter in greater detail.

The augmented reality device user interface 304 is used to receive user input from and/or for providing system output to the user (for example, the medical procedure personnel) or to one or more devices. The augmented reality device user interface 304 includes one or more input devices, including but not limited to a navigation key, a function key, a microphone, a voice recognition component, joystick, or any other mechanism capable of receiving an input from a user now known or in the future developed, or any combination thereof. Further, the augmented reality device user interface 304 includes one or more output devices, including but not limited to a speaker, headphones, display, or any other mechanism capable of presenting an output to a user now known or in the future developed, or any combination thereof. In some embodiments, the augmented reality device user interface 304 includes a user interface mechanism such as a touch interface or gesture detection mechanism that allows a user to interact with the displayed elements of the augmented reality device display 322 or projected into the eyes of the user.

As illustrated, an augmented reality device display 322 is a separate user interface or combined within the augmented reality device user interface 304. The augmented reality device display 322 provides a two-dimensional or three-dimensional image visible to the wearer of the augmented reality device 104. The augmented reality device display 322 is, for example, a projection device for displaying information such as text, images, graphics, or video received from the computing device 102 via the network 106 of FIG. 1. In some embodiments, the augmented reality device user interface 304 further includes, for example, a serial port, a parallel port, an infrared (IR) interface, a universal serial bus (USB) interface and/or any other interface herein known or in the future developed.

The augmented reality device network interface 306 is used to enable the augmented reality device 104 to communicate on a network, such as, the network 106 of FIG. 1, a wireless access network (WAN), a radio frequency (RF) network, and the like. In an embodiment, the augmented reality device network interface 306 includes, for example, an Ethernet card or adapter or a wireless local area network (WLAN) card or adapter. Additionally, or alternatively, the augmented reality device network interface 306 includes a radio frequency interface for wide area communications such as Long-Term Evolution (LTE) networks, or any other network now known or in the future developed. In some embodiments, the augmented reality device network interface 306 includes address, control, and/or data connections to enable appropriate communications on the network.

The augmented reality device memory 310 includes any non-transitory memory elements comprising one or more of volatile memory elements (for example, random access memory (RAM), nonvolatile memory elements (for example, read-only memory "ROM"), and combinations thereof). Moreover, in some embodiments, the augmented reality device memory 310 incorporates electronic, magnetic, optical, and/or other types of storage media now known or in the future developed. Note that, in an embodiment, the augmented reality device memory 310 has a distributed architecture, where various components are situated remotely from one another but are accessed by the augmented reality device processor 308. The software in the augmented reality device memory 310 includes one or more software programs, each of which includes an ordered listing of executable instructions for implementing logical functions. The software in the augmented reality device memory 310 includes a suitable augmented reality device operating system 314 and one or more augmented reality device applications 316. The augmented reality device operating system 314 controls the execution of other computer programs, such as, the one or more augmented reality device applications 316, and provides scheduling, input-output control, file and data management, memory management, and communication control and related services. The one or more augmented reality device applications 316 are configured to implement the various processes, algorithms, methods, techniques, and the like described herein.

The augmented reality device memory 310 includes an experience module 326 that is executed by the augmented reality device processor 308 to implement the various processes, algorithms, methods, techniques, and the like described herein. The augmented reality device memory 310 further includes an augmented reality device data storage 312 used to store data. In the exemplary embodiment of FIG. 3, the augmented reality device data storage 312 is located internal to the augmented reality device memory 310 of the augmented reality device 104. Additionally, or alternatively, the augmented reality device data storage 312 are located external to the augmented reality device 104 such as, for example, an external hard drive connected to the augmented reality device user interface 304 (not shown). In a further embodiment, the augmented reality device data storage 312 are located external and connected to the augmented reality device 104 through a network and accessed via the augmented reality device network interface 306 (not shown). In some embodiments, when the connection between the computing device 102 and the augmented reality device 104 is an intermittent connection, the data is stored in the augmented reality device data storage 312. Alternatively, when the connection between the computing device 102 and the augmented reality device 104 is constant (i.e., not intermittent), the data is stored within one or more of the augmented reality device data storage 312, any memory external to the augmented reality device 104, and/or distributed thereto.

In operation, information for storage in the augmented reality device data storage 312 is entered via the augmented reality device user interface 304. Alternatively, information for storage in the augmented reality device data storage 312 is received from the computing device 102 via the augmented reality device transceiver 302. Alternatively, information for storage in the augmented reality device data storage 312 is received from one or more sensors (not shown) external to the augmented reality device 104 via the augmented reality device transceiver 302. Alternatively, information for storage in the augmented reality device data storage 312 is received from one or more augmented reality device sensors 324. For example, the position data, and the like is stored in the augmented reality device data storage 312.

The augmented reality device 104 includes the augmented reality device transceiver 302. The augmented reality device transceiver 302 incorporated within an augmented reality device transceiver antenna (not shown), enables wireless communication between the augmented reality device 104 and other devices, for example, the computing device 102 of FIG. 1. It will be appreciated by those of ordinary skill in the art that the augmented reality device 104 includes a single augmented reality device transceiver 302 as shown, or alternatively separate transmitting and receiving components, for example but not limited to, a transmitter, a transmitting antenna, a receiver, and a receiving antenna and/or any combination thereof.

The augmented reality device 104 in the illustrated example includes one or more augmented reality device sensors 324. The one or more augmented reality device sensors 324 detect the spatial information corresponding to the physical characteristics of the medical procedure room. It will be appreciated by those of ordinary skill in the art that the one or more augmented reality device sensors 324 include any sensor technology now known or in the future developed. For example, the one or more augmented reality device sensors 324 include one or more of a Light Detection and Ranging (LiDAR) sensor, a Quick Response (QR) code reader, a Radio Detection and Ranging (RADAR) sensor, ultrasonic sensors, three-dimensional (3D) scanner, IoT (Internet of Things) sensors, RFID (radio frequency identification) sensors, image sensors (for example, camera), biometric sensors, and various other sensors known in the art or developed in the future. In some embodiments, the augmented reality device sensors 324 are physically within, co-located, or external to the augmented reality device 104. In some embodiments, the one or more augmented reality device sensors 324 include sensors such as accelerometers, gyroscopes, and magnetometers to track the orientation and movement of the augmented reality device 104. Each of the one or more augmented reality device sensors 324 comprises a detector allowing the detection of the spatial characteristics of the physical characteristics of the medical procedure room and/or various medical items contained within. In some embodiments, the one or more augmented reality device sensors 324, such as QR code readers, provide detection and tracking of the various medical items within the medical procedure room. In operation, the one or more augmented reality device sensors 324 communicate with one another, with other sensors within the medical procedure room, and/or with any other device within or external to the medical procedure room.

The detailed functions and operations of the computing device 102 and the augmented reality device 104 will now be detailed herein. Although the description below discusses the functions and operations performed by the respective computing device 102 and augmented reality device 104, a person skilled in the art would appreciate that, in some embodiments, the functions and operations of the computing device 102 and the augmented reality device 104 are performed in a single device or in a distributed manner by two or more devices without limiting the scope of the claimed subject matter.

Figure 4A:
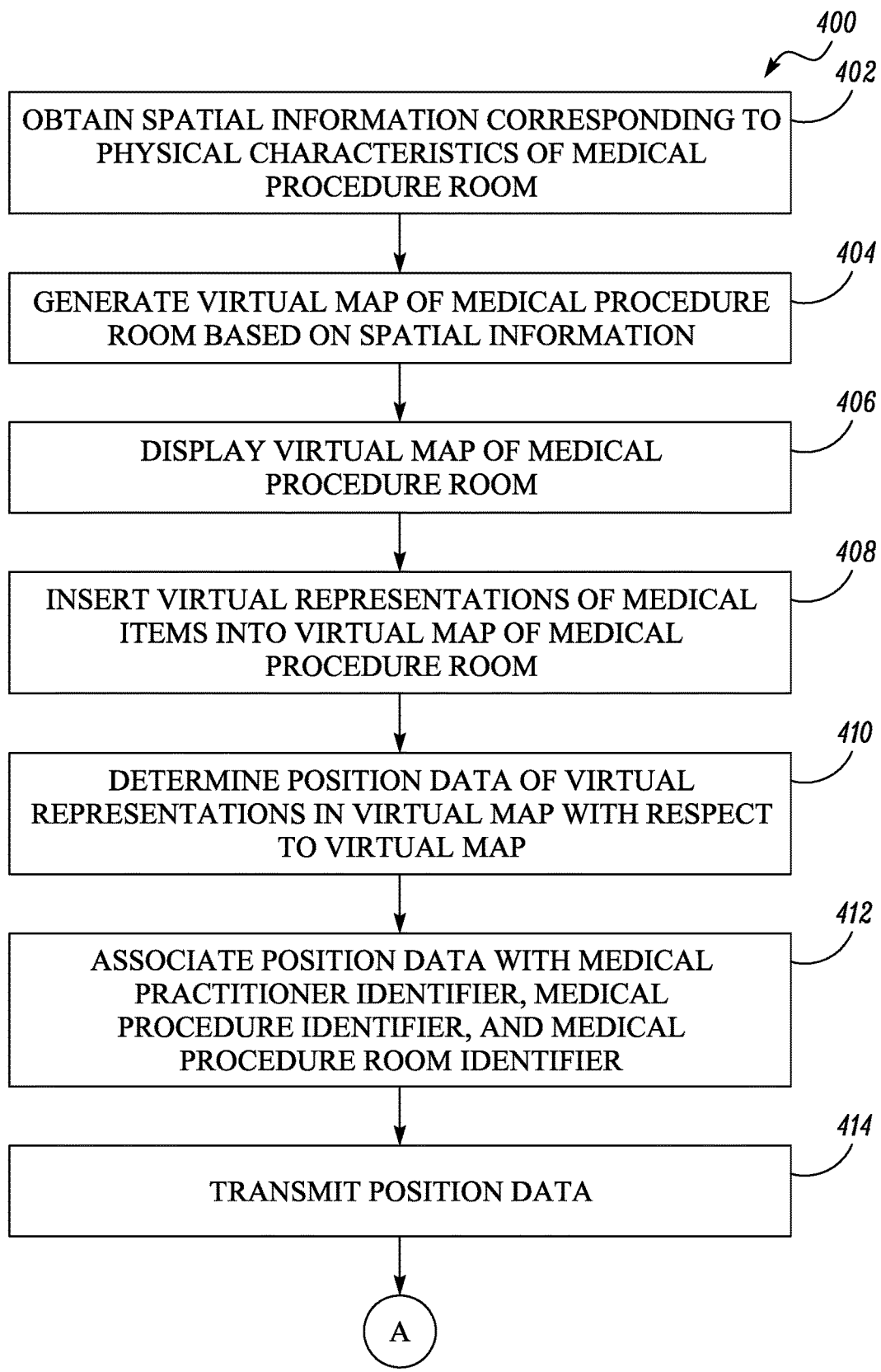
FIGS. 4A through 4B depict a flow diagram of a method for managing the medical procedure room for the medical procedure, in accordance with some embodiments.
Figure 4B:
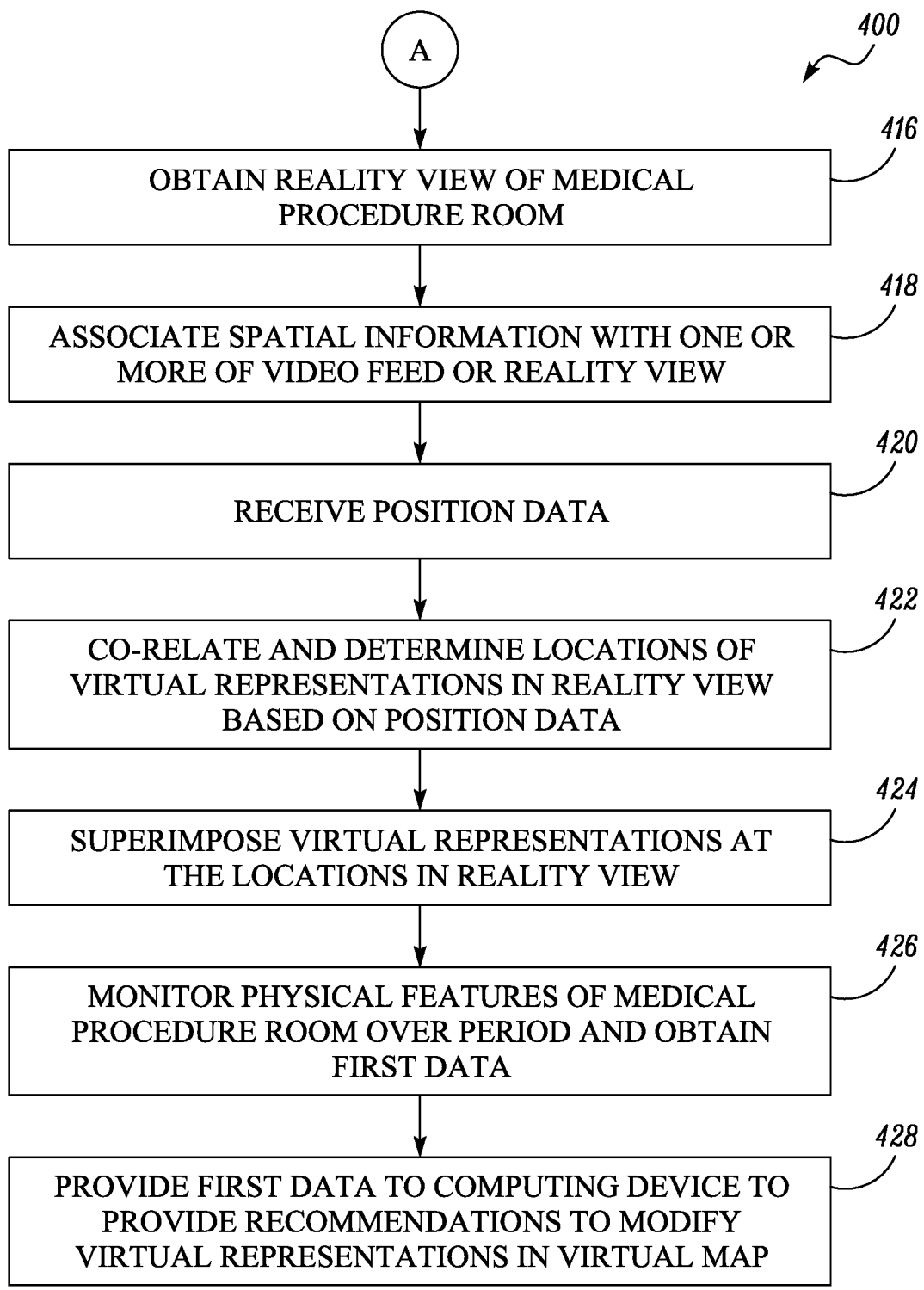
Figure 5:
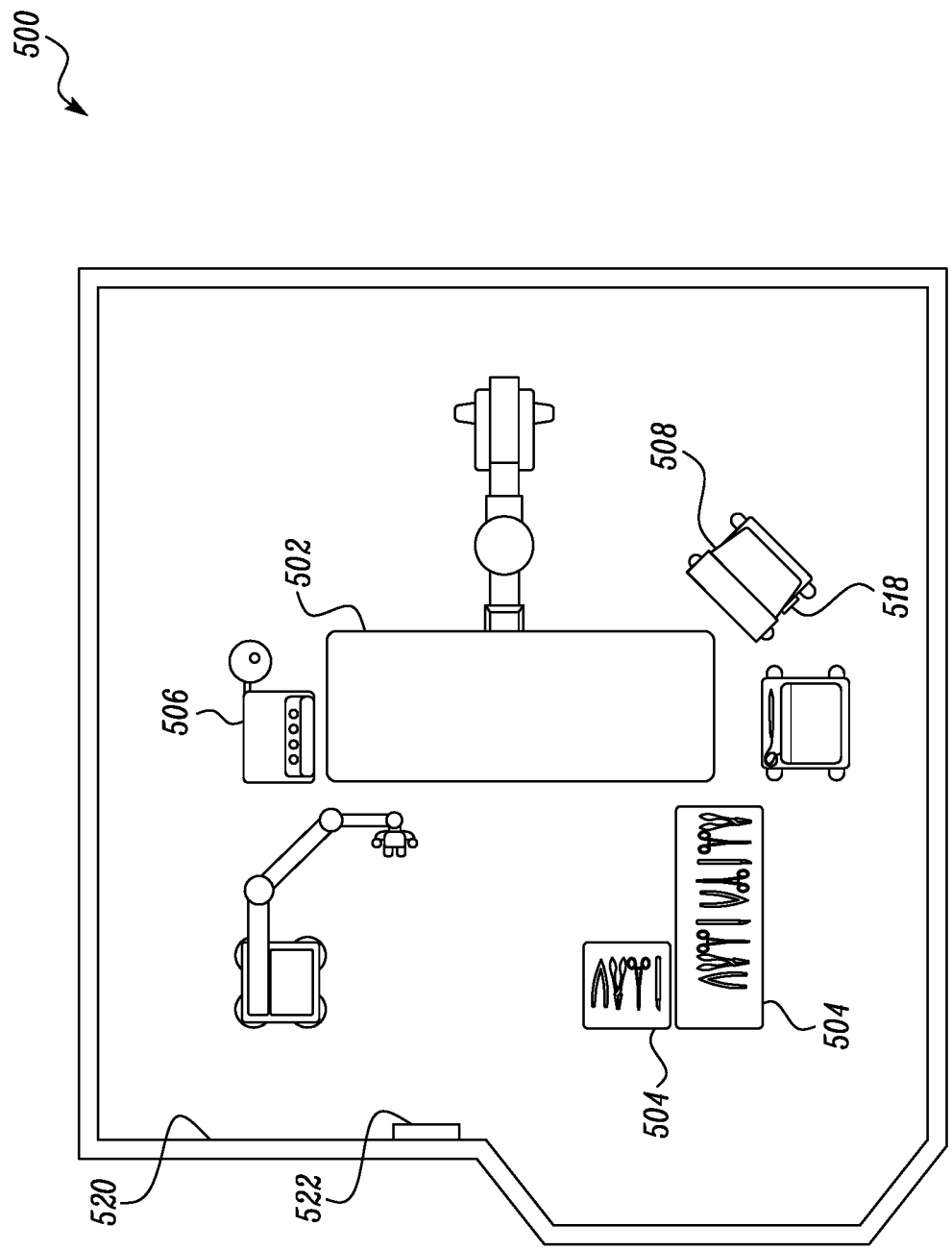
FIG. 5 is a plan view of an exemplary medical procedure room, in accordance with some embodiments.

FIG. 4 is a flow diagram of method 400 for managing a medical procedure room for a medical procedure, in accordance with some embodiments. As shown in FIG. 5, in an exemplary embodiment, the medical procedure room 500 includes medical items, such as, a medical procedure table 502, one or more auxiliary tables 504, a back table 506, an enabling technology system 508, and other medical items for use within the medical procedure room that are now known or in the future developed. In some embodiments, one or more digital markers, such as, Quick Response (QR) codes or other visual markers, are placed on one or more walls and/or the medical items in the medical procedure room 500. For example, a first marker 522 is placed on a first wall 520 and a second marker 518 is placed on the enabling technology system 508, as shown in FIG. 5. It will be understood that the medical procedure room 500 is not limited to the medical items shown in FIG. 5, and includes any number of items of equipment, electronic devices, imaging devices, surgical robots or other systems, lights, or any other devices and/or supplies preferred or required by a medical practitioner and/or other medical procedure room personnel for use in a medical procedure now known or in the future developed.

At 402, the method 400 begins with the computing device 102 (for example, the computing device processor 208) executing the creator module 222 to obtain a spatial information corresponding to physical characteristics of the medical procedure room 500. In accordance with various embodiments, the spatial information includes physical dimensions (for example, length, width, and height) and layout of the medical procedure room 500. For example, at 402, the computing device 102 determines the length, width, height, and the layout of the seven (7) walls exemplarily provided in the medical procedure room 500, as shown in FIG. 5. The computing device 102 obtains the spatial information from one or more of the computing device sensors 220, such as, LiDAR, RADAR, 3D scanner, image sensors, and the like. In some alternate embodiments, the computing device 102 obtains the spatial information from the one or more sensors external to the computing device 102, such as, the augmented reality device sensors 324. It will be appreciated by a person skilled in the art that the spatial information of the medical procedure room is determined using various techniques known in the art, the details of which are not described here for the sake of brevity.

In some embodiments, the computing device 102 also obtains information associated with the marker, for example, the first marker 522 placed on the first wall 520 of the medical procedure room 500, as shown in FIG. 5. The information associated with the marker includes spatial information associated with the placement of the marker on the wall, identification of the wall on which the marker is placed, and the content of the marker. For example, the spatial information includes, but is not limited to, the position of the marker on the wall, and the height from the floor of the medical room at which the marker is placed. The information is obtained using the one or more of the computing device sensors 220 and/or the augmented reality device sensors 324. In some embodiments, the spatial information and the identification of the wall is manually entered by a user, such as, the medical practitioner or the medical procedure room personnel.

Referring back to FIG. 4, at 404, the computing device 102 executes the creator module 222 to generate a virtual map of the medical procedure room based on the spatial information. The virtual map of the medical procedure room includes virtual representation of the one or more walls of the medical procedure room arranged according to the layout. In accordance with various embodiments, the generation of the virtual map includes creating the virtual representation of the one or more walls of the medical procedure room based on the obtained physical dimensions and layout of the medical procedure room. The virtual map of the medical procedure room is generated based on various techniques or mapping software applications, the details of which are not described for the sake of brevity. The virtual representation of the one or more walls in the virtual map is a scaled-down representation of the one or more walls of the medical procedure room proportional to the actual dimensions of the wall.

Figure 6:
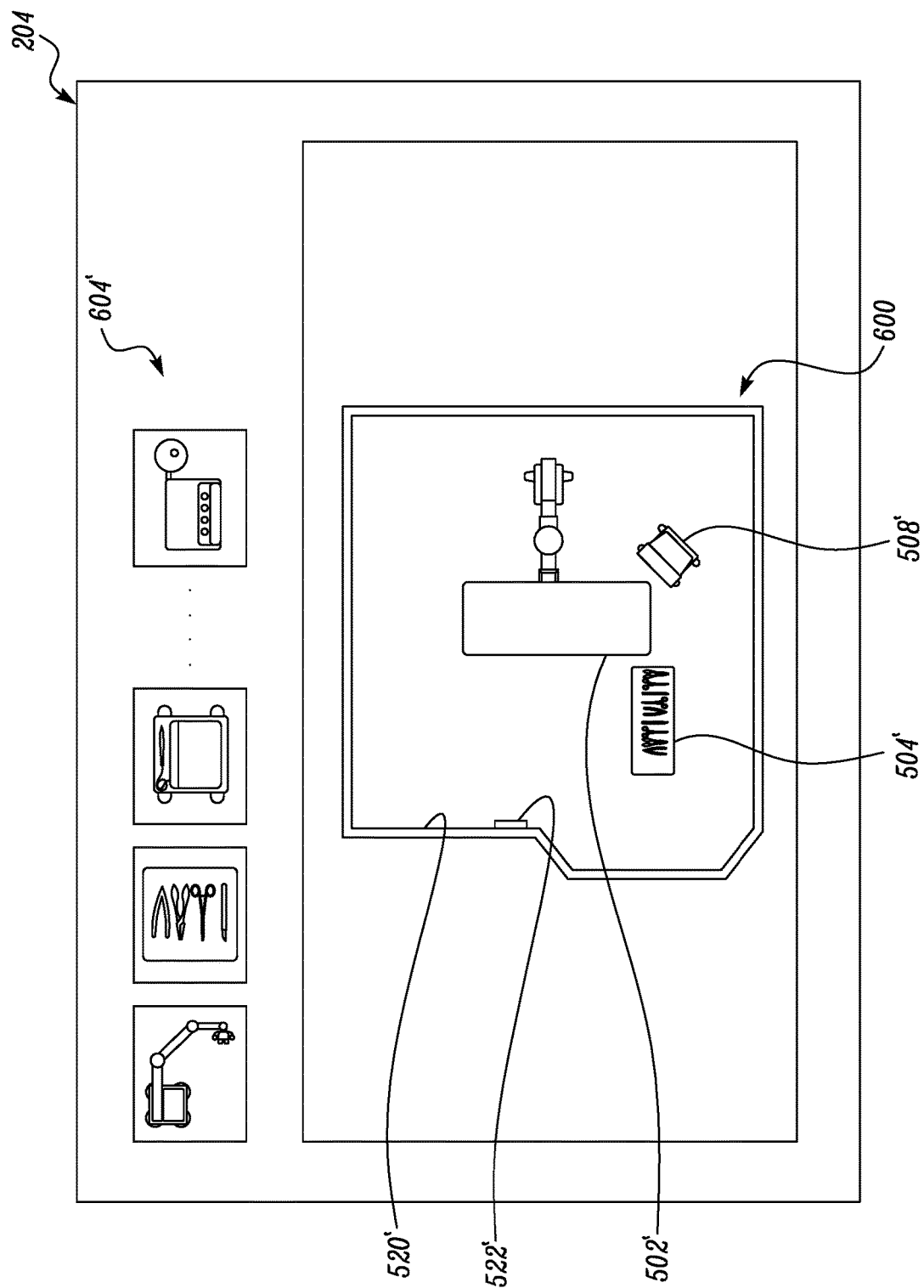
FIG. 6 is a view of an exemplary virtual map of the medical procedure room, in accordance with some embodiments.

At 406, the computing device 102 executes the creator module 222 to display the virtual map of the medical procedure room on the display device, for example, the computing device user interface 204 of the computing device 102. For example, at 404, the computing device 102 generates the virtual map 600 of the medical procedure room 500 and, at 406, the computing device 102 displays the virtual map 600 on the computing device user interface 204 as shown in FIG. 6. In some embodiments, the virtual map 600 also displays a virtual representation 522' of the first marker 522 in the virtual map 600 on the virtual representation 520' of the first wall 520 of the medical procedure room 500. In accordance with various embodiments, each virtual representation (for example, the virtual representations 520', 522') is a scaled down representation of the corresponding wall and the item (for example, the first wall 520 and the marker 522) in the medical procedure room 500.

Referring back to FIG. 4, at 408, the computing device 102 executes the creator module 222 to insert one or more virtual representations of one or more medical items into the virtual map of the medical procedure room in response to one or more commands. The one or more commands include a request to position the virtual representations in the virtual map. The virtual representation is a two-dimensional or a three-dimensional representation of the one or more medical items. To this end, the computing device 102 obtains the one or more virtual representations of the one or more medical items from the computing device memory 210 or other devices, such as, the augmented reality device 104. As shown in FIG. 6, the computing device 102 displays the one or more virtual representations 604' of the medical items on the computing device user interface 204, for example, on the computing device display, for selection by the medical practitioner and/or other medical procedure room personnel.

In some embodiments, the computing device 102 identifies the virtual representation of the desired medical item from the displayed virtual representations 604', for example, based on the one or more commands from the user and displays the identified virtual representations 604' on the computing device user interface 204. The computing device 102 then enables the user to select and insert the virtual representations 604' of the medical items at desired locations in the virtual map 600. The desired locations for the virtual representations 604 depend on the preferences of a medical practitioner performing the medical procedure in the medical procedure room. For example, the virtual representations 502, 504, 508' of the medical procedure table 502, the auxiliary table 504 and the enabling technology system 508 respectively, are inserted in the virtual map 600 at desired locations based on the one or more commands from a user. The insertion of the virtual representations 604 of the medical items at the desired locations in the virtual map 600 is done using various techniques, such as, keyboard shortcuts, drag and drop method, copy-paste method, and various other methods now known or in the future developed. In some embodiments, the computing device 102 provides one or more recommendations for the auto insertion of the virtual representations 604 of the medical items in the virtual map 600 to the user based on previous instances of set-up of medical procedure room, as will be described in greater detail with reference to FIG. 9.

Referring back to FIG. 4, at 410, the computing device 102 executes the creator module 222 to determine position data of the one or more virtual representations in the virtual map with respect to the virtual map. In accordance with various embodiments, the position data of the virtual representation of the medical items represent the position and orientation of the virtual representation of the medical item in the virtual map with respect to the virtual map. In an embodiment, the position data of the virtual representation in the virtual map with respect to the virtual map is determined by including a coordinate system to ascertain the placement of the virtual representations. For example, the computing device 102 establishes a coordinate system by setting an origin point within the virtual map and determines the coordinates of the virtual representation by measuring its position relative to the origin point in the virtual map. For example, the computing device 102 considers the virtual representation 522 of the first marker 522 as the origin point and determines the coordinates of the virtual representations by measuring its position relative to the virtual representation 522 of the first marker 522 in the virtual map 600.

At 412, the computing device 102 executes the creator module 222 to associate the position data with one or more of a medical practitioner identifier identifying the medical practitioner, a medical procedure identifier identifying the medical procedure, and a medical procedure room identifier identifying the medical procedure room. As an example, the computing device 102 determines that the user inserting the virtual representations is one and the same person/medical practitioner(s) associated with these identifiers. Alternatively, the computing device 102 determines that the user inserting the virtual representations is a different medical personnel than that associated with these identifiers. The computing device 102 obtains the medical practitioner identifier, the medical procedure identifier, and the medical procedure room identifier via the computing device user interface 204 from the user, for example, the medical procedure room personnel or the medical practitioner. In accordance with various embodiments, the position data is stored as a preference card associated with one or more of the medical practitioner identifier, the medical procedure identifier, and the medical procedure room identifier in the computing device data storage 212. In some embodiments, the process is repeated to create multiple preference cards associated with a medical practitioner identifier depending upon the medical procedure and/or the medical procedure room. For example, the medical procedure room personnel creates different preference cards for two different types of medical procedures for a medical practitioner, as the set-up requirements for the different medical procedures for the same medical practitioner are different. Additionally, the medical procedure room personnel creates different preference cards for a medical practitioner for two different medical procedure rooms with different layouts. In some embodiments, the process is repeated for a plurality of medical practitioners.

At 414, the computing device 102 executes the creator module 222 to transmit the position data associated with the medical practitioner identifier, the medical procedure identifier, and the medical procedure room identifier, via the computing device transceiver 202, to the augmented reality device 104.

At 416, the augmented reality device 104 (for example, the augmented reality device processor 308) executes the experience module 326 to obtain a reality view of the medical procedure room. As discussed above, the reality view of the medical procedure room includes a direct or indirect view of the medical procedure room obtained using the one or more augmented reality device sensors 324. The augmented reality device 104 also aligns the direct or indirect view of the medical procedure room based on the orientation and movement of the augmented reality device 104 received from the augmented reality device sensors 324, such as, accelerometers, gyroscopes, and magnetometers.

The augmented reality device 104 obtains one or more of the medical practitioner identifier, the medical procedure identifier, and the medical procedure room identifier from the user via the augmented reality device user interface 304. The augmented reality device 104 further obtains the spatial information corresponding to the medical procedure room identified by the medical procedure room identifier from the computing device 102. Further, at 418, the augmented reality device 104 executes the experience module 326 to associate the spatial information with the reality view of the medical procedure room. To this end, the augmented reality device 104 determines the dimensions and layout of one or more walls of the medical procedure room that are visible in the reality view of the augmented reality device 104. It would be appreciated that the dimensions and layout of the one or more walls of the medical procedure room can be determined by the augmented reality device 104 using various techniques now known in the art or in the future developed. The augmented reality device 104 then compares the determined dimensions and layout of the one or more walls with the spatial information (including the dimensions of the walls) to associate the corresponding spatial information with the one or more walls. For example, when the dimensions of a wall viewed using the augmented reality device 104 match the spatial information of the first wall 520 (shown in FIG. 5) of the medical procedure room 500, the augmented reality device 104 identifies the wall viewed using the augmented reality device 104 as the first wall 520 and associates the spatial information of the first wall 520 with the viewed wall. The above process is repeated for all walls of the medical procedure room. In some embodiments, the augmented reality device 104 associates the spatial information with the other walls viewed in the reality view based on the relative positioning of the other walls with respect to the first wall 520.

In some embodiments, the augmented reality device 104 associates the spatial information with the reality view by using an origin point, such as, the first marker 522 placed on the first wall 520 of the medical procedure room 500 (shown in FIG. 5). To this end, the augmented reality device sensors 324 scans the first marker 522 placed on the first wall 520 of the medical procedure room 500 and provide the spatial information and the content of the first marker 522 to the augmented reality device 104. The augmented reality device 104 identifies the first marker 522 based on the content of the first marker 522 and uses the positioning information of the first marker 522 as a reference point to associate the spatial information with the reality view of the augmented reality device 104. It would be appreciated that the association of the spatial information with the reference point can be done using various techniques now known in the art or in the future developed.

At 420, the augmented reality device 104 executes the experience module 326 to receive the position data via the augmented reality device transceiver. At 422, the augmented reality device 104 executes the experience module 326 to co-relate and determine locations of the one or more virtual representations in the reality view based on the position data, using various techniques now known in the art or in the future developed. At 424, the augmented reality device 104 executes the experience module 326 to superimpose, on an augmented reality device display 322, the one or more virtual representations at the locations in the reality view. For example, the augmented reality device 104 identifies the markers, such as the markers 518, 522 in the medical procedure room and uses the markers as the reference points for superimposing virtual representations of the medical items at the determined locations in the reality view. In accordance with various embodiments, the superimposed virtual representation corresponds to the actual dimensions of the medical item.

The augmented reality device 104 determines whether the positioning of the medical item placed in the medical procedure room corresponds to the superimposed virtual representation of the medical item. To this end, the augmented reality device 104 identifies one or more medical items, such as, the medical procedure table 502, auxiliary tables 504, the back table 506, and the enabling technology system 508 (shown in FIG. 5), in the medical procedure room 500. As an example, the augmented reality device 104 identifies the medical items by detecting and tracking the markers placed on the medical items in the real time. A person skilled in the art would appreciate that the identification of one or more medical items by an augmented reality device is done by a variety of techniques now known or in the future developed.

Figure 7:
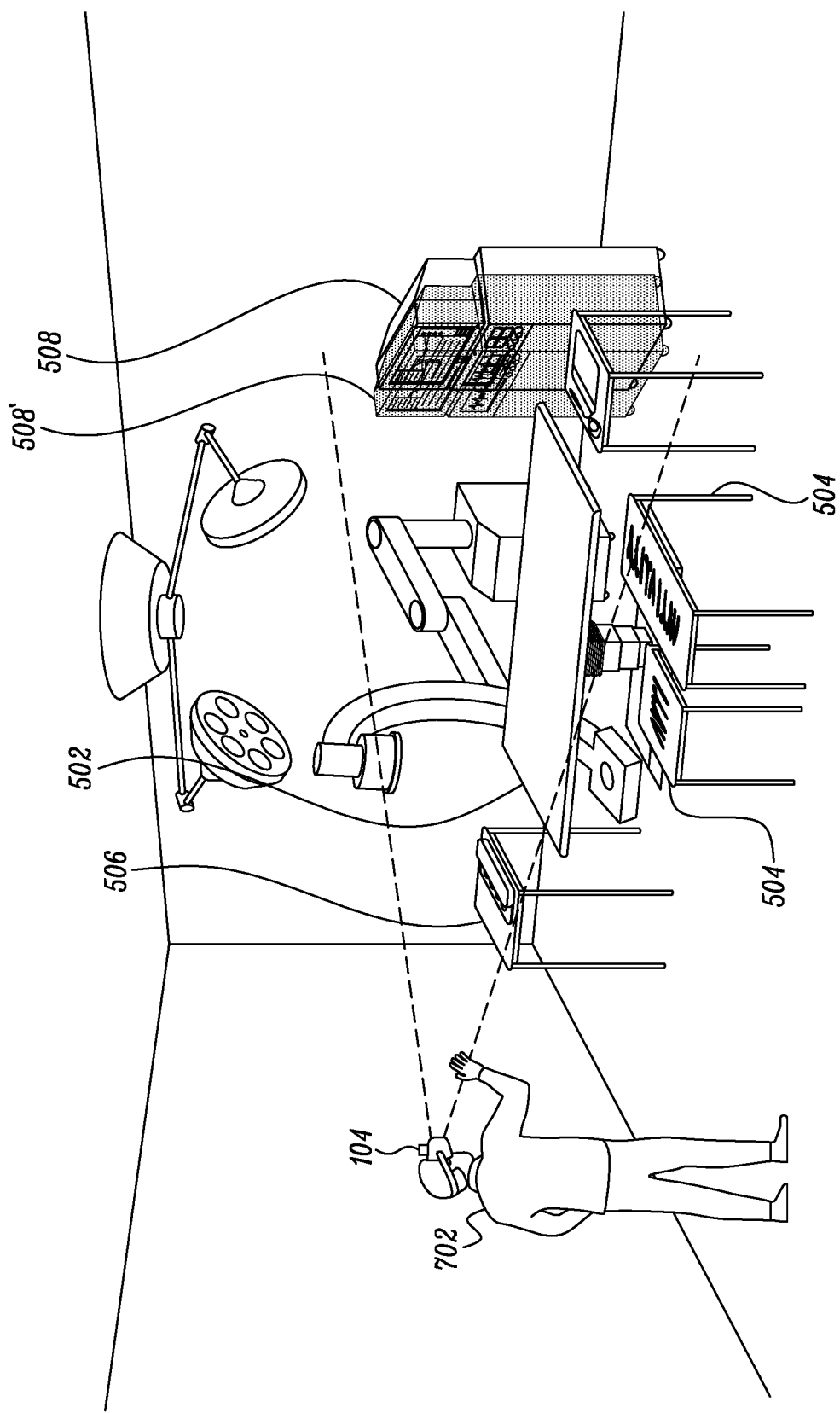
FIGS. 7 through 8 are views of the exemplary medical procedure room from the augmented reality device, in accordance with some embodiments.
Figure 8:
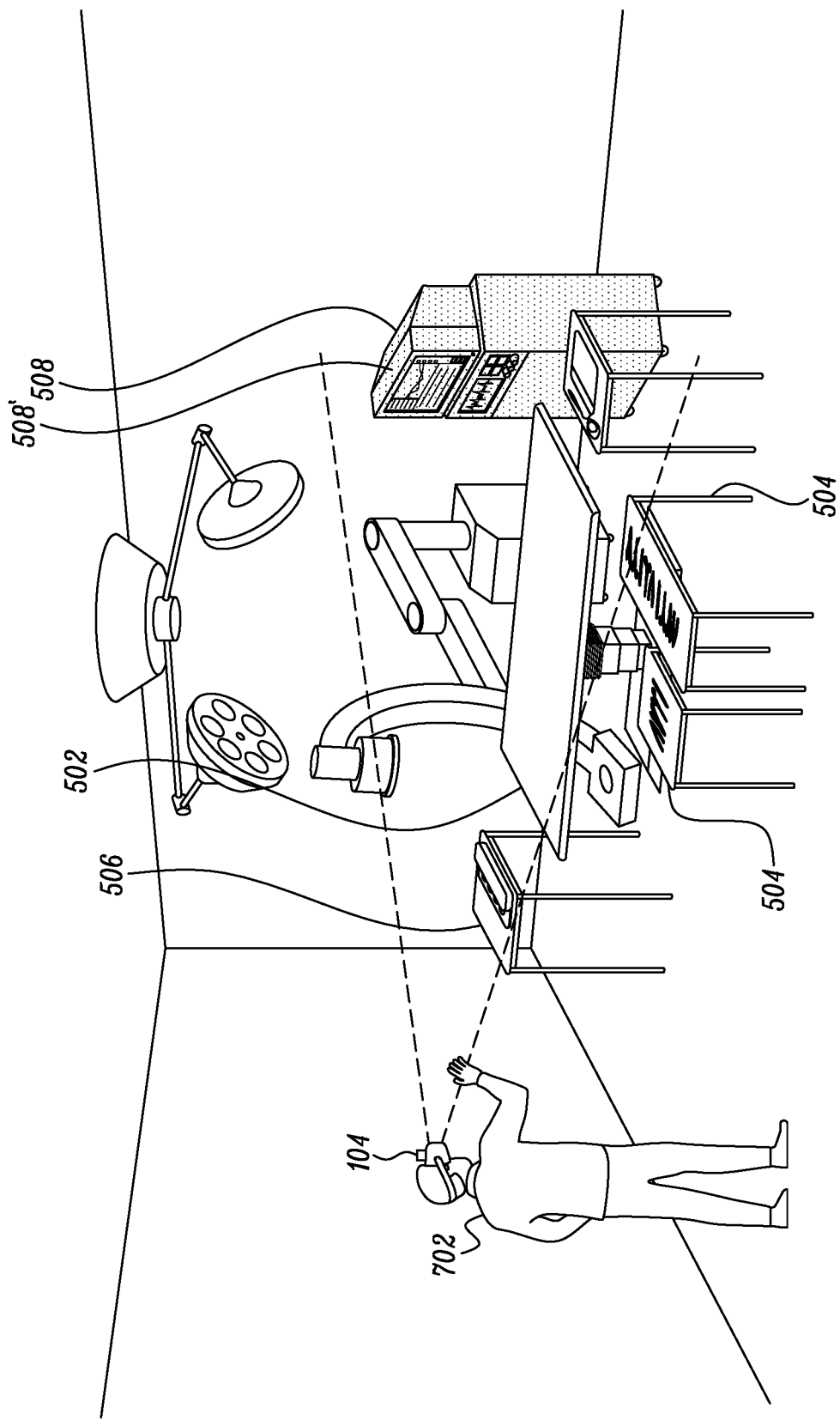

The augmented reality device 104 upon determining that the positioning of the medical item placed in the medical procedure room does not correspond to the superimposed virtual representation of the medical item, provides an indication to the user to match the positioning of the medical item with the superimposed virtual representation. It would be appreciated that the determination of whether the positioning of the medical item placed in the medical procedure room corresponds to the superimposed virtual representation of the medical item is done by the augmented reality device 104 using various techniques now known in the art or in the future developed. The indication includes an audio or a visual indication. For example, as shown in FIG. 7, when the positioning of the enabling technology system 508 does not match the virtual representation 508' of the enabling technology system 508, the augmented reality device 104 provides an indication on the augmented reality device 104, to the user 702 to match the positioning of the enabling technology system 508 with the superimposed virtual representation 508' of the enabling technology system 508, as shown in FIG. 8.

At 426, the augmented reality device 104 executes the experience module 326 to monitor physical features of the medical procedure room and obtain a first data. In some embodiments, the physical features are monitored over a period for which the medical practitioner performs the medical procedure in the medical procedure room. The monitoring of physical features includes monitoring the movement, positioning, and orientation of the medical items in the medical procedure room. At 428, the augmented reality device 104 executes the experience module 326 to, pursuant to a lapse of the period, provide via the augmented reality device transceiver 302 the first data to the computing device 102 (for example, the creator module 222 of the computing device 102) to provide recommendations, on the computing device display, to optimize the positioning of the one or more virtual representations in the virtual map of the medical procedure room. In some embodiments, the augmented reality device 104 provides recommendations in real-time to optimize the positioning of the one or more virtual representations in the virtual map of the medical procedure room, based on the monitored physical features. In accordance with various embodiments, the optimization includes modification of the positioning of the one or more virtual representations in the virtual map of the medical procedure room corresponding to one or more of the medical practitioner identifier, the medical procedure identifier, and the medical procedure room identifier. The optimization of the positioning of the one or more virtual representations in the virtual map will now be described in greater detail below.

Figure 9:
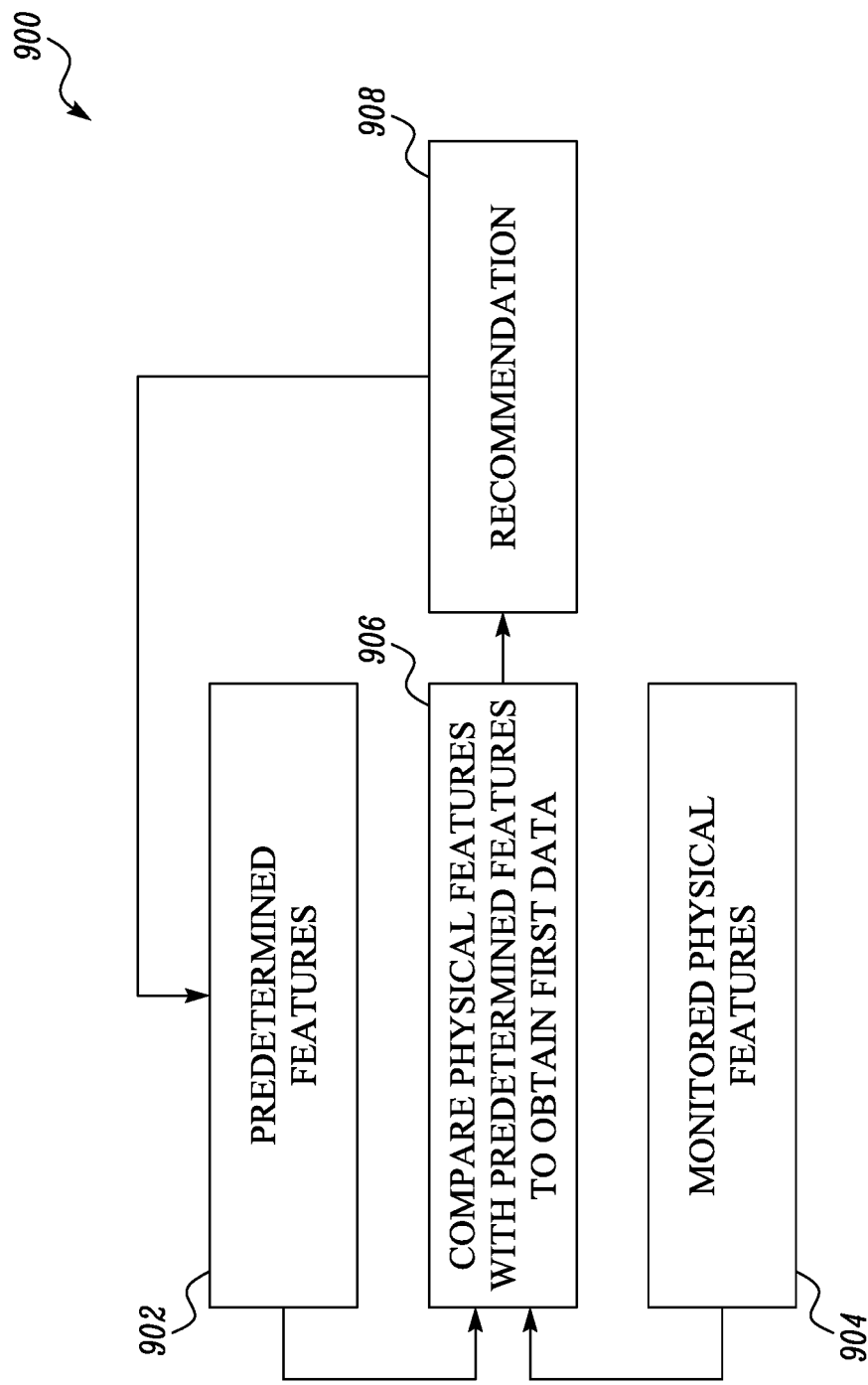
FIG. 9 is a block diagram of an optimization cycle for use within the augmented reality device, in accordance with some embodiments.

Referring to FIG. 9, the optimization cycle 900 associated with the positioning of the one or more virtual representations in the virtual map is described. At 902, the augmented reality device 104 executes the experience module 326 to receive the predetermined features from the computing device 102. In an embodiment, the predetermined features are stored in the computing device memory 210 and the computing device 102 obtains the predetermined features from the computing device memory 210 and transmits it to the augmented reality device 104. In accordance with various embodiments, the predetermined features correspond to the physical features of the medical procedure room monitored for one or more durations occurring prior to the period. In an embodiment, the one or more durations include one or more first durations for which the medical practitioner performs the medical procedure in the medical procedure room. In some other embodiments, the one or more durations include one or more second durations associated with one or more of a plurality of medical practitioner identifiers, a plurality of medical procedure identifiers, and a plurality of medical procedure room identifiers.

At 904, the augmented reality device 104 executes the experience module 326 to monitor physical features of the medical procedure room over the period for which the medical practitioner performs the medical procedure in the medical procedure room. The monitoring of physical features includes monitoring the movement, positioning, and orientation of the medical items in the medical procedure room, for example, based on the detection and tracking of the markers, such as QR codes, placed on the medical items in the medical procedure room.

At 906, the augmented reality device 104 executes the experience module 326 to compare the physical features 902 of the medical procedure room monitored over the period with the predetermined features 904 to obtain the first data. To this end, the augmented reality device 104 arrives at compared data based on the comparison of the physical features of the medical procedure room monitored over the period with the predetermined features. At this stage, the augmented reality device 104 determines at least one of an omission of one or more medical items from the medical procedure room, an addition of one or more medical items in the medical procedure room, and a change in an actual position of the one or more medical items in the medical procedure room during the period based on the compared data. For example, the augmented reality device 104 determines the omission of one or more medical items from the medical procedure room based on the absence of the corresponding markers of the medical items from the medical procedure room. The augmented reality device 104 determines the addition of one or more medical items in the medical procedure room based on the addition of the corresponding markers of the medical items in the medical procedure room. The augmented reality device 104 determines the change in an actual position of the one or more medical items in the medical procedure room based on the change in the positioning of the corresponding markers of the medical items in the medical procedure room.

At 908, the augmented reality device 104 executes the experience module 326 to, pursuant to a lapse of the period, provide via the augmented reality device transceiver the first data to the computing device 102 (for example, the creator module 222 of the computing device 102) to provide recommendations, on the computing device display, to modify the one or more virtual representations in the virtual map of the medical procedure room corresponding to the medical practitioner identifier, the medical procedure identifier, and the medical procedure room identifier. In accordance with various embodiments, the recommendations include recommendations to remove one or more virtual representations from the virtual map based on the omission of one or more medical items from the medical procedure room during the period, recommendations to add one or more virtual representations in the virtual map based on the addition of one or more medical items in the medical procedure room during the period, and recommendations to alter the position data of the one or more virtual representations in the virtual map to a new position data in the virtual map based on the change in the actual position of the one or more medical items in the medical procedure room data during the period. In some embodiments, the recommendations include, but not limited to, reference guide to position the medical items, surgical technique to use the medical item, and the like.

The augmented reality device 104 includes any machine learning module configured to learn and adapt itself to continuous improvement in changing environments. The augmented reality device 104 employs any one or combination of the following computational techniques: neural network, constraint program, fuzzy logic, classification, conventional artificial intelligence, symbolic manipulation, fuzzy set theory, evolutionary computation, cybernetics, data mining, approximate reasoning, derivative-free optimization, decision trees, and/or soft computing. The augmented reality device 104 implements an iterative learning process. The learning is based on a wide variety of learning rules or training algorithms. In an embodiment, the learning rules include one or more of back-propagation, patter-by-pattern learning, supervised learning, and/or interpolation. The augmented reality device 104 is configured to implement one or more machine learning algorithms to provide recommendations to modify the positioning of the one or more virtual representations of the medical items based on the previous instances of the medical procedure room set up. In accordance with some embodiments of the invention, the machine learning algorithm utilizes any machine learning methodology, now known or in the future developed, for classification. For example, the machine learning methodology utilized includes one or a combination of: Linear Classifiers (Logistic Regression, Naive Bayes Classifier); Nearest Neighbor; Support Vector Machines; Decision Trees; Boosted Trees; Random Forest; and/or Neural Networks. The augmented reality device 104 continually evolves the specifics of set up of the medical procedure room in real time with new data inputs. The machine learning intent is to continually implement optimized medical procedure room set up over time.

The optimization cycle 900, for example, is implemented within the augmented reality device 104 of FIG. 3. In an alternative embodiment, the optimization cycle 900 is implemented as a cloud-based internet program accessed by the augmented reality device 104. In yet another alternative embodiment, the optimization cycle 900 is distributively implemented within a system in which the various components are remotely located from each other in other embodiments and accessed by the augmented reality device 104.

The system and the method of the present disclosure are directed towards the management of a medical procedure room by enabling the user to achieve an accurate set-up of the medical items in the medical procedure room. In the present disclosure, the preferred position data of each medical item within the medical procedure room is determined by enabling the user to insert the virtual representation of the medical items in the virtual map of the medical procedure room using simple techniques, such as, drag and drop method. By superimposing the virtual representation of the medical items on the corresponding actual medical items present in the medical procedure room, the present disclosure enables the user to accurately adjust the positioning of the actual medical items in the medical procedure room based on the preferred position data. Moreover, the system and the method of the present disclosure optimize the management of the medical procedure room by providing recommendations to the users to modify the positioning of the virtual representations of the medical items in the virtual map based on the previous instances of set-up of the medical items. This will also reduce the time in training medical procedure room personnel for setting up the medical procedure room.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover, in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element preceded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (for example, comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

The invention claimed is:

1. A system for managing a medical procedure room for a medical procedure, the system comprising:
   a computing device configured to execute a creator module to:
      obtain a spatial information corresponding to physical characteristics of the medical procedure room;
      generate a virtual map of the medical procedure room based on the spatial information;
      display, on a computing device display, the virtual map of the medical procedure room;
      insert, via a computing device user interface, one or more virtual representations of one or more medical items into the virtual map of the medical procedure room in response to one or more commands;

determine position data of the one or more virtual representations in the virtual map with respect to the virtual map;

associate the position data with a medical practitioner identifier identifying the medical practitioner, a medical procedure identifier identifying the medical procedure, and a medical procedure room identifier identifying the medical procedure room;

obtain predetermined features from a computing device memory; and transmit, via a computing device transceiver, the predetermined features, and the position data associated with the medical practitioner identifier, the medical procedure identifier, and the medical procedure room identifier; and an augmented reality device communicatively coupled to the computing device, the augmented reality device configured to execute an experience module to:

obtain a reality view of the medical procedure room;

associate the spatial information with the reality view of the medical procedure room;

receive, via an augmented reality device transceiver, the predetermined features and the position data;

co-relate and determine locations of the one or more virtual representations in the reality view based on the position data;

superimpose, on an augmented reality device display, the one or more virtual representations at the locations in the reality view;

monitor physical features of the medical procedure room over a period for which the medical practitioner performs the medical procedure in the medical procedure room, and obtain a first data, wherein to obtain the first data:

compare the physical features of the medical procedure room monitored over the period with the predetermined features received from the computing device and arrive at a compared data; and determine at least one of:

an omission of one or more medical items from the medical procedure room during the period based on the compared data, an addition of one or more medical items in the medical procedure room during the period based on the compared data, and a change in an actual position of the one or more medical items in the medical procedure room during the period based on the compared data; and pursuant to a lapse of the period, provide via the augmented reality device transceiver the first data to the computing device to provide recommendations, on the computing device display, to modify the one or more virtual representations in the virtual map of the medical procedure room corresponding to the medical practitioner identifier, the medical procedure identifier, and the medical procedure room identifier, wherein providing recommendations to modify the one or more virtual representations in the virtual map includes providing recommendations to remove one or more virtual representations from the virtual map based on the omission of one or more medical items from the medical procedure room during the period.

2. The system of claim 1, wherein providing recommendations to modify the one or more virtual representations in the virtual map includes providing recommendations to add one or more virtual representations in the virtual map based on the addition of one or more medical items in the medical procedure room during the period.

3. The system of claim 1, wherein providing recommendations to modify the one or more virtual representations in the virtual map includes providing recommendations to alter the position data of the one or more virtual representations in the virtual map to a new position data in the virtual map based on the change in the actual position of the one or more medical items in the medical procedure room data during the period.

4. The system of claim 1, wherein the predetermined features correspond to the physical features of the medical procedure room monitored for one or more first durations for which the medical practitioner performs the medical procedure in the medical procedure room, wherein the one or more first durations occur prior to the period.

5. The system of claim 1, wherein the predetermined features correspond to the physical features of the medical procedure room monitored for one or more second durations associated with one or more of a plurality of medical practitioner identifiers, a plurality of medical procedure identifiers, and a plurality of medical procedure room identifiers, wherein the one or more second durations occur prior to the period.

6. The system of claim 1, further comprising:
one or more sensors configured to detect the spatial information corresponding to the physical characteristics of the medical procedure room.

7. The system of claim 6, wherein the sensor includes one or more sensors from a group comprising of a Light Detection and Ranging (LiDAR) sensor, a Radio Detection and Ranging (RADAR), ultrasonic sensors, three-dimensional (3D) scanner, and a camera.

8. The system of claim 1, wherein the position data includes orientation of the one or more virtual representations of the one or more medical items in the virtual map with respect to the virtual map.

9. The system of claim 1, wherein the virtual representation is a three-dimensional representation of the one or more medical items.

10. A method for managing a medical procedure room for a medical procedure, the method comprising:

obtaining, by a computing device, a spatial information corresponding to physical characteristics of the medical procedure room;

generating, by the computing device, a virtual map of the medical procedure room based on the spatial information;

displaying, by the computing device, the virtual map of the medical procedure room on a computing device display;

inserting, by the computing device, one or more virtual representations of one or more medical items into the virtual map of the medical procedure room in response to one or more commands;

determining, by the computing device, position data of the one or more virtual representations in the virtual map with respect to the virtual map;

associating, by the computing device, the position data with a medical practitioner identifier identifying the medical practitioner, a medical procedure identifier identifying the medical procedure, and a medical procedure room identifier identifying the medical procedure room;

obtaining, by the computing device, predetermined features from a computing device memory; and transmitting, by the computing device, the predetermined features and the position data associated with the medical practitioner identifier, the medical procedure identifier, and the medical procedure room identifier via a computing device transceiver;

obtaining, by an augmented reality device, a reality view of the medical procedure room;

associating, by the augmented reality device, the spatial information with the reality view of the medical procedure room;

receiving, by the augmented reality device, the predetermined features and the position data via an augmented reality device transceiver;

co-relating and determining, by the augmented reality device, locations of the one or more virtual representations in the reality view based on the position data;

superimposing, by the augmented reality device, the one or more virtual representations at the locations in the reality view on an augmented reality device display;

monitoring, by the augmented reality device, physical features of the medical procedure room over a period for which the medical practitioner performs the medical procedure in the medical procedure room and obtaining a first data wherein obtaining the first data includes:

comparing, by the augmented reality device, the physical features of the medical procedure room over the period with the predetermined features of the medical procedure room associated with the medical practitioner identifier, the medical procedure identifier, and the medical procedure room identifier and arrive at a compared data; and determining, by the augmented reality device, at least one of:

an omission of one or more medical items from the medical procedure room during the period based on the compared data, an addition of one or more medical items in the medical procedure room during the period based on the compared data, and a change in an actual position of the one or more medical items in the medical procedure room during the period based on the compared data; and pursuant to a lapse of the period, providing, by the augmented reality device, the first data to the computing device to provide recommendations on the computing device display to modify the one or more virtual representations in the virtual map of the medical procedure room corresponding to the medical practitioner identifier, the medical procedure identifier, and the medical procedure room identifier, wherein providing recommendations to modify the one or more virtual representations in the virtual map includes providing recommendations to remove one or more virtual representations from the virtual map based on the omission of one or more medical items from the medical procedure room during the period.

11. The method of claim 10, wherein providing recommendations to modify the one or more virtual representations in the virtual map includes providing recommendations to add one or more virtual representations in the virtual map based on the addition of one or more medical items in the medical procedure room during the period.

12. The method of claim 10, wherein providing recommendations to modify the one or more virtual representations in the virtual map includes providing recommendations to alter the position data of the one or more virtual representations in the virtual map to a new position data in the virtual map based on the change in the actual position of the one or more medical items in the medical procedure room data during the period.

13. The method of claim 10, wherein the predetermined features correspond to the physical features of the medical procedure room monitored for one or more first durations for which the medical practitioner performs the medical procedure in the medical procedure room, wherein the one or more first durations occur prior to the period.

14. The method of claim 10, wherein the predetermined features correspond to the physical features of the medical procedure room monitored for one or more second durations associated with one or more of a plurality of medical practitioner identifiers, a plurality of medical procedure identifiers, and a plurality of medical procedure room identifiers, wherein the one or more second durations occur prior to the period.

15. The method of claim 10, further comprising:
detecting, by one or more sensors, the spatial information corresponding to the physical characteristics of the medical procedure room.

16. The method of claim 10, wherein the position data includes orientation of the one or more virtual representations of the one or more medical items in the virtual map with respect to the virtual map.

* * * * *